(12) United States Patent
Yoshii et al.

(10) Patent No.: US 11,754,066 B2
(45) Date of Patent: Sep. 12, 2023

(54) PUMP SYSTEM, FLUID SUPPLY DEVICE AND PRESSURE DETECTION METHOD

(71) Applicant: MINEBEA MITSUMI INC., Nagano (JP)

(72) Inventors: Yuta Yoshii, Tokyo (JP); Chikara Sekiguchi, Tokyo (JP); Shigenori Inamoto, Tokyo (JP); Yuki Takahashi, Tokyo (JP); Daisuke Kodama, Tokyo (JP); Daisuke Kurita, Nagano (JP)

(73) Assignee: MINEBEA MITSUMI INC., Nagano (JP)

( * ) Notice: Subject to any disclaimer, the term of this patent is extended or adjusted under 35 U.S.C. 154(b) by 0 days.

(21) Appl. No.: 17/645,577

(22) Filed: Dec. 22, 2021

(65) Prior Publication Data
US 2022/0205444 A1     Jun. 30, 2022

(30) Foreign Application Priority Data
Dec. 25, 2020   (JP) ................................. 2020-218020

(51) Int. Cl.
*F04B 49/08*   (2006.01)
*F04B 45/047*  (2006.01)
*F04B 49/06*   (2006.01)

(52) U.S. Cl.
CPC ............ *F04B 49/08* (2013.01); *F04B 45/047* (2013.01); *F04B 49/06* (2013.01)

(58) Field of Classification Search
CPC ........ F04B 49/08; F04B 49/06; F04B 45/047; F04B 43/046
See application file for complete search history.

(56) References Cited

U.S. PATENT DOCUMENTS

| 2005/0019180 | A1* | 1/2005 | Seto ..................... F04B 43/046 417/413.1 |
| 2007/0208258 | A1* | 9/2007 | Whitaker ............... A61B 5/021 600/490 |
| 2007/0243084 | A1* | 10/2007 | Vogeley ................ F04B 43/046 417/413.2 |
| 2007/0267940 | A1* | 11/2007 | Wright .................. F04B 43/046 310/311 |
| 2014/0257116 | A1 | 9/2014 | Kobayashi et al. |

(Continued)

FOREIGN PATENT DOCUMENTS

| EP | 2607699 A1 | 6/2013 |
| JP | 2013220321 A | 10/2013 |
| JP | 2014184701 A | 10/2014 |

(Continued)

OTHER PUBLICATIONS

European Patent Office, Extended European Search Report Issued in Application No. 21216139.2, dated May 25, 2022, Germany, 12 pages.

*Primary Examiner* — Connor J Tremarche
(74) *Attorney, Agent, or Firm* — McCoy Russell LLP

(57) ABSTRACT

A pump system contains a vibration actuator which can be electromagnetically driven, a sealed chamber connected to a suction port and a discharge port, and a movable wall for changing a volume of the sealed chamber. The movable wall is displaced due to drive of the vibration actuator to supply fluid in the sealed chamber into a cuff. The pump system detects pressure in the cuff based on a consumption current of the vibration actuator.

8 Claims, 8 Drawing Sheets

(56) References Cited

U.S. PATENT DOCUMENTS

2016/0038699 A1* 2/2016 Higashiyama .... A61M 16/0003
128/207.15
2017/0306935 A1 10/2017 Fujiwara

FOREIGN PATENT DOCUMENTS

| JP | 2015146894 A | 8/2015 |
| JP | 2017209433 A | 11/2017 |

* cited by examiner

PUMP SYSTEM, FLUID SUPPLY DEVICE AND PRESSURE DETECTION METHOD

CROSS-REFERENCE TO RELATED APPLICATION

The present application claims priority to Japanese Patent Application No. 2020-218020 filed on Dec. 25, 2020. The entire contents of the above-listed application is hereby incorporated by reference for all purposes.

TECHNICAL FIELD

The present disclosure relates to a pump system, a fluid supply device and a pressure detection method.

BACKGROUND

Each of patent document 1, patent document 2 and patent document 3 describes an electronic sphygmomanometer for measuring a blood pressure value of a user. The electronic sphygmomanometer has a configuration including a cuff attached to an arm of the user, a pump for supplying air into the cuff to increase pressure in the cuff and a pressure sensor for detecting the pressure in the cuff.

RELATED ART DOCUMENTS

Patent Documents

JP 2015-146894A
JP 2014-184071A
JP 2017-209433A

SUMMARY

Problem to be Solved

As described above, the electronic sphygmomanometer disclosed in each of the patent documents 1, 2 and 3 has the configuration in which the pressure sensor is provided as a different component separated from the pump. Thus, there is a problem that the number of components of the electronic sphygmomanometer becomes large and the size of the electronic sphygmomanometer also becomes large.

The present disclosure has been made in view of the above-described problem of the conventional art. Accordingly, it is an object of the present disclosure to provide a pump system which can be miniaturized by employing a configuration in which the pressure sensor is omitted and the pressure in the cuff can be detected by using the pump, a fluid supply device containing the pump system and a pressure detection method performed by the pump system.

Means for Solving the Problem

The above object is achieved by the present disclosures defined in the following (1) to (7).

(1) A pump system, comprising:
a vibration actuator which can be electromagnetically driven;
a sealed chamber connected to a suction port and a discharge port; and
a movable wall for changing a volume of the sealed chamber,
wherein the movable wall is displaced due to drive of the vibration actuator to supply fluid in the sealed chamber into a target object, and
wherein pressure in the target object is detected based on a consumption current of the vibration actuator.

(2) The pump system according to the above (1), wherein the vibration actuator is configured so that a resonant frequency of the vibration actuator changes according to the pressure in the target object.

(3) The pump system according to the above (2), wherein the vibration actuator has a fluid spring formed from elastic force of the fluid in the sealed chamber, and
wherein the resonance frequency changes when a spring constant of the fluid spring changes according to the pressure in the target object.

(4) The pump system according to the above (2) or (3), wherein the consumption current monotonically changes in a reducing direction or an increasing direction as the pressure in the target object increases.

(5) The pump system according to the above (4), wherein the consumption current linearly changes.

(6) A fluid supply device, comprising:
the pump system defined by any one of the above (1) to (5).

(7) A pressure detection method performed by a pump system containing a vibration actuator which can be electromagnetically driven, a sealed chamber connected to a suction port and a discharge port, and a movable wall for changing a volume of the sealed chamber, wherein the movable wall is displaced due to drive of the vibration actuator to supply fluid in the sealed chamber into a target object, the pressure detection method comprising:
detecting pressure in the target object based on a consumption current of the vibration actuator.

Effects of the Invention

The pump system of the present disclosure can detect the pressure in the target object based on the consumption current of the vibration actuator which can be electromagnetically driven. Thus, it is possible to detect the pressure in the target object without using any pressure sensor. Therefore, it is possible to reduce the number of components of the pump system and reduce the size of the pump system.

The fluid supply device of the present disclosure contains the above-described pump system. Therefore, the fluid supply device can receive the effect of the pump system and thus it is possible to reduce the size of the fluid supply device.

Further, the pressure detection method of the present disclosure can detect the pressure in the target object based on the consumption current of the vibration actuator which can be electromagnetically driven. Thus, it is possible to detect the pressure in the target object without using any pressure sensor. Therefore, it is possible to reduce the number of components of the pump system and reduce the size of the pump system.

DETAILED DESCRIPTION

Hereinafter, a pump system, a fluid supply device and a pressure detection method of the present disclosure will be described in detail with reference to a preferred embodiment shown in the accompanying drawings.

Figure 1:
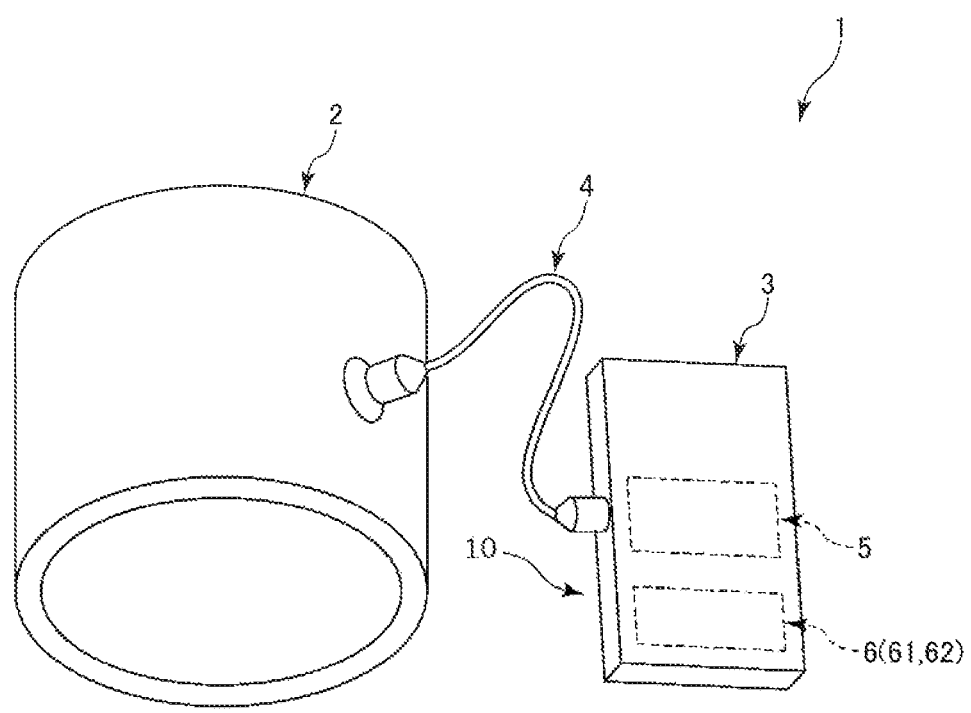
FIG. 1 is a perspective view showing an overall configuration of an electronic sphygmomanometer according to a preferred embodiment.
Figure 2:
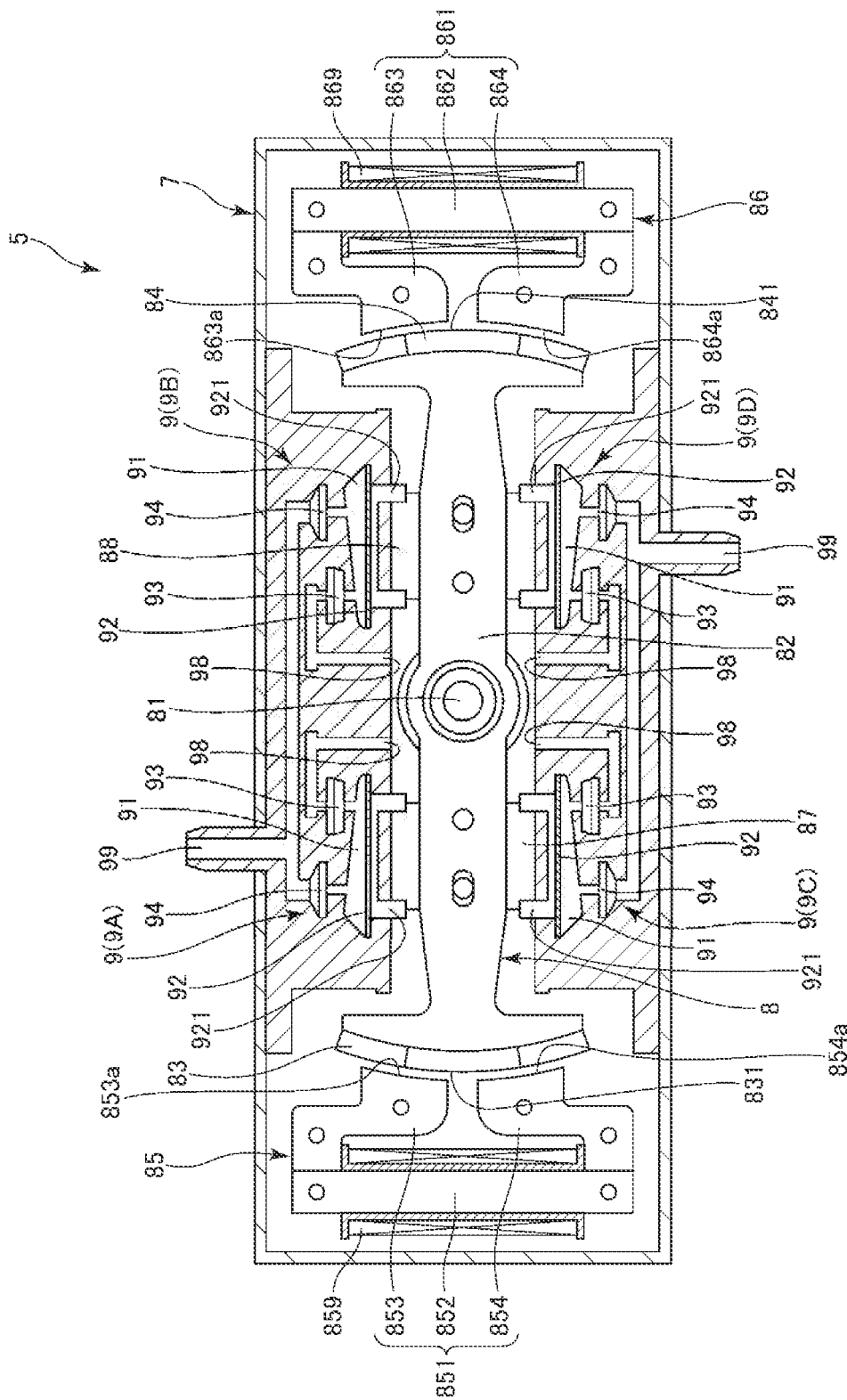
FIG. 2 is a cross-sectional view of a pump.
Figure 3:
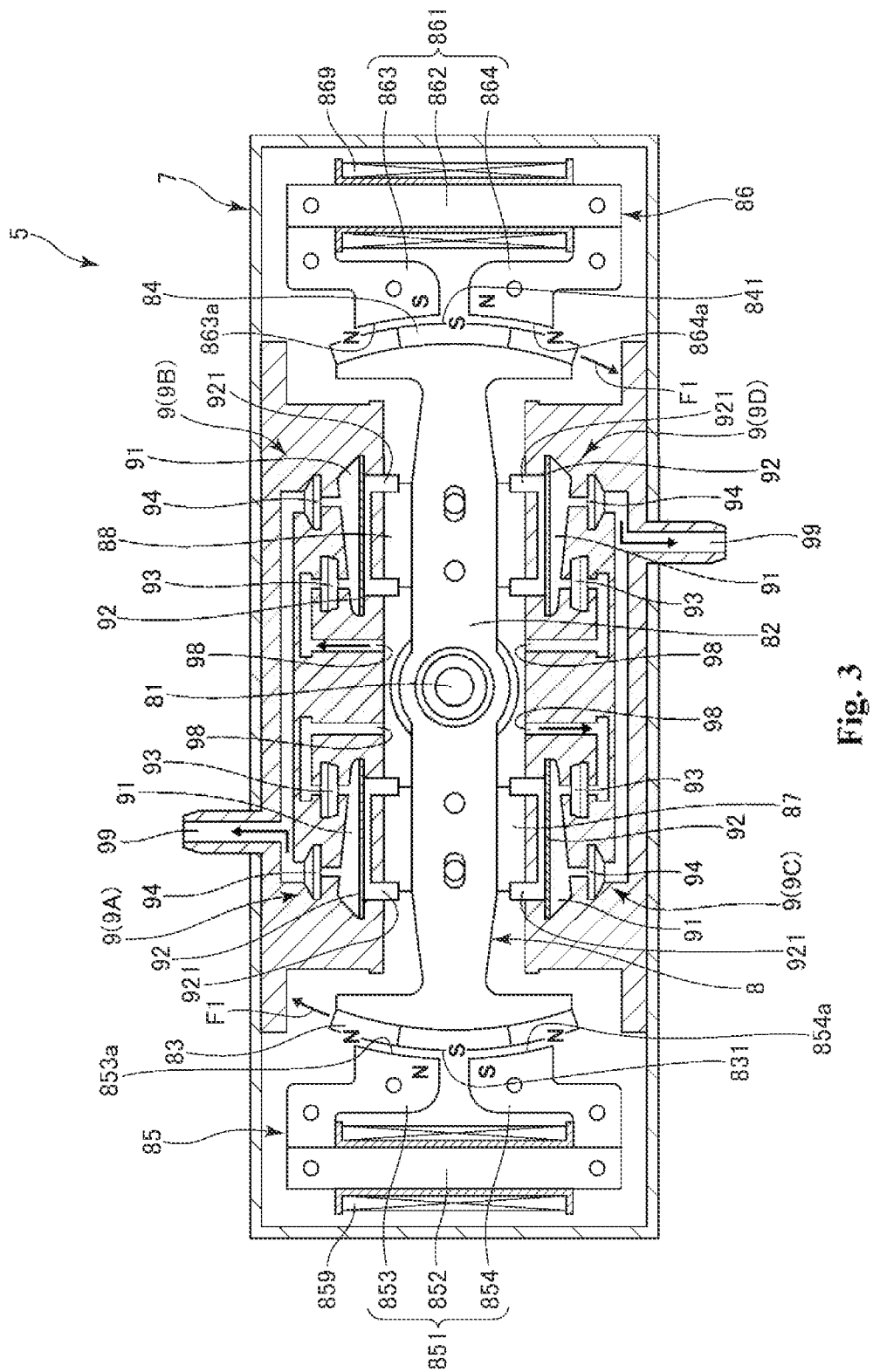
FIG. 3 is a cross-sectional view showing a driving principle of the pump shown in FIG. 2.
Figure 4:
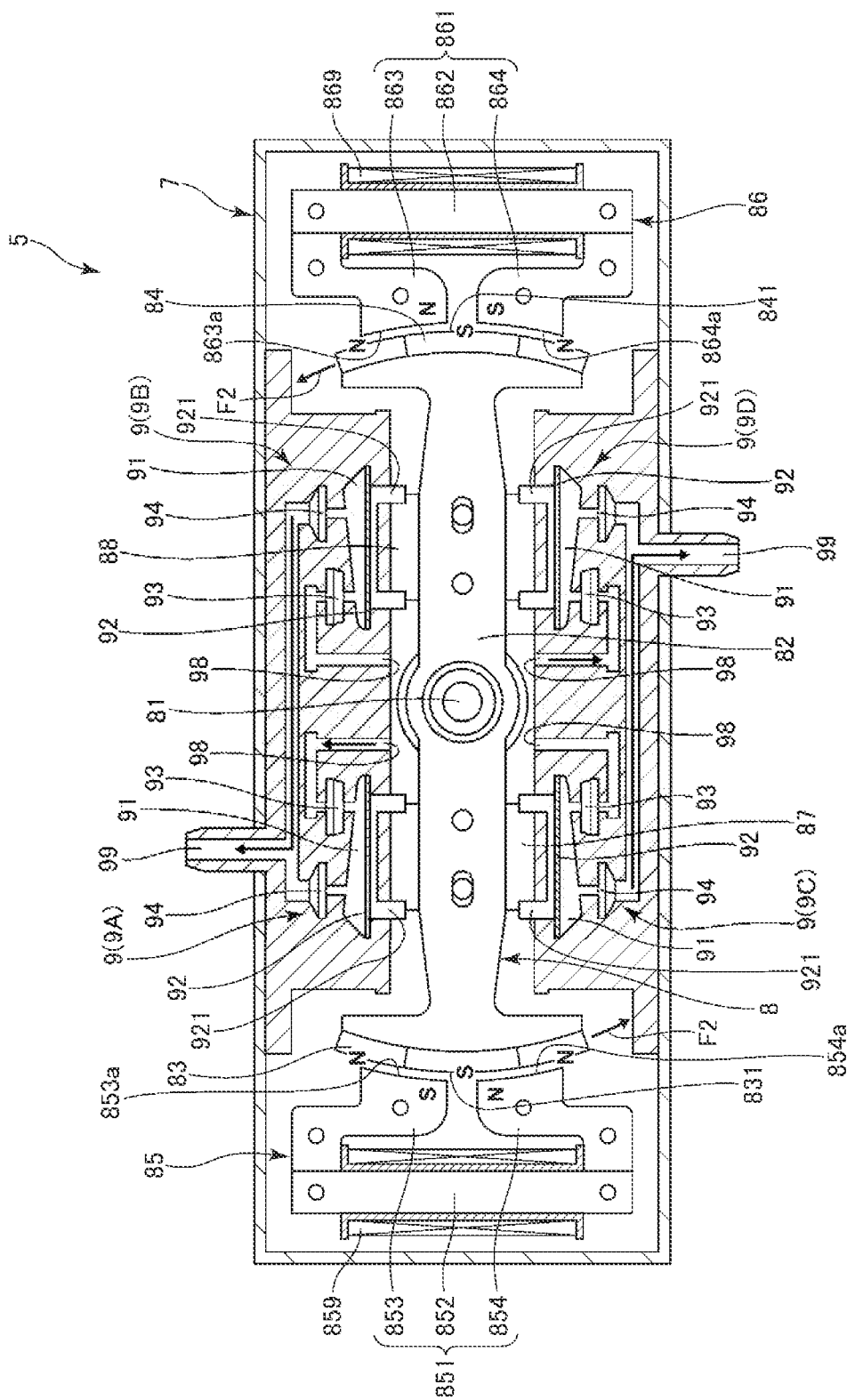
FIG. 4 is another cross-sectional view showing the driving principle of the pump shown in FIG. 2.
Figure 5:
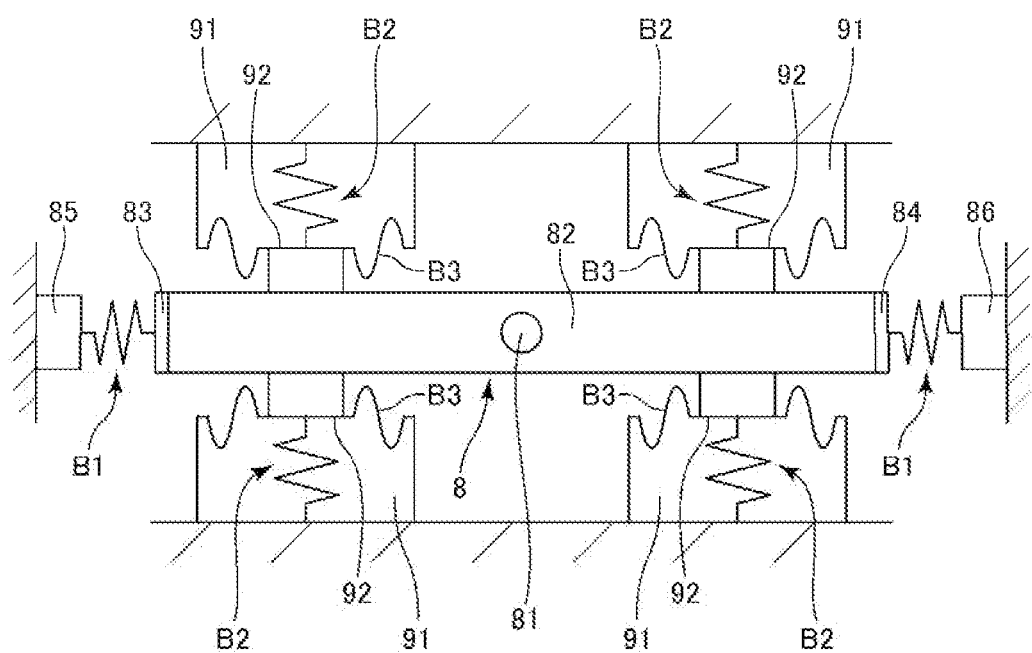
FIG. 5 is a schematic diagram showing a spring system of a vibration actuator.
Figure 6:
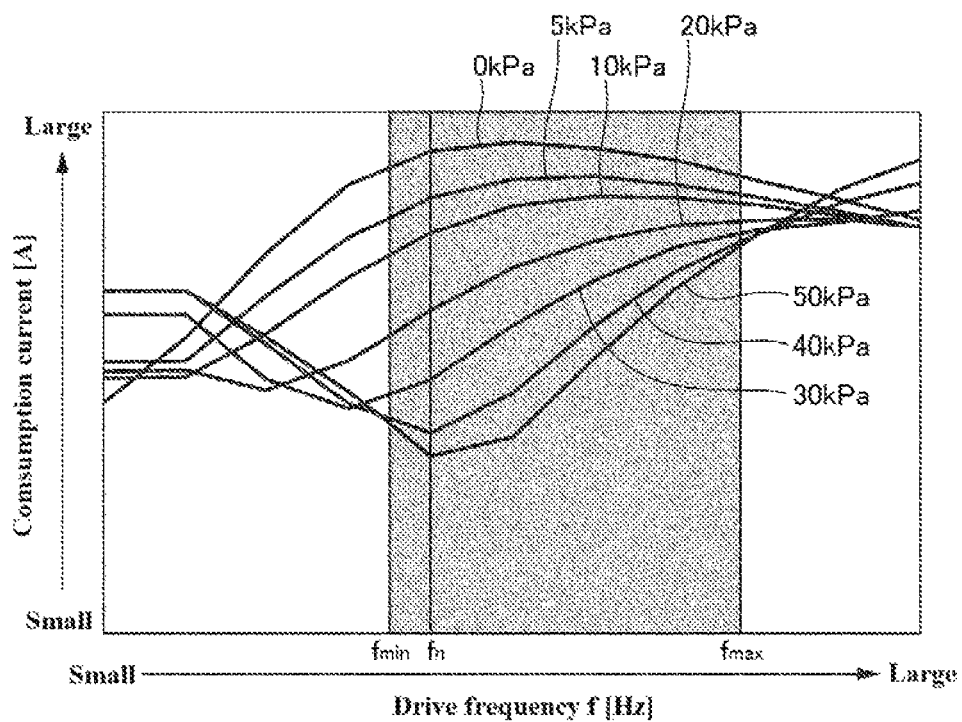
FIG. 6 is a graph showing a relationship between a drive frequency and a consumption current of the vibration actuator.

FIG. 1 is a perspective view showing an overall configuration of an electronic sphygmomanometer according to the preferred embodiment. FIG. 2 is a cross-sectional view of a pump. FIG. 3 is a cross-sectional view showing a driving principle of the pump shown in FIG. 2. FIG. 4 is another cross-sectional view showing the driving principle of the pump shown in FIG. 2. FIG. 5 is a schematic diagram showing a spring system of a vibration actuator. FIG. 6 is a graph showing a relationship between a drive frequency and a consumption current of the vibration actuator. FIGS. 7 to 11 are graphs respectively showing different relationships between pressure in a sealed chamber and the consumption current. In the following description, an upper side of the paper on which each of FIGS. 2 to 4 is illustrated is sometimes referred to as "an upper side" and a lower side of the paper on which each of FIGS. 2 to 4 is illustrated is sometimes referred to as "a lower side" for convenience of explanation.

FIG. 1 shows an electronic sphygmomanometer 1 serving as a fluid supply device. The electronic sphygmomanometer 1 includes a cuff 2, a main body 3 and a tube 4 for connecting between the cuff 2 and the main body 3 to supply and discharge fluid. The cuff 2 is attached to a measurement target part such as an arm of a user. The cuff 2 has a bladder provided therein. The bladder is inflated when the fluid is supplied from the main body 3 into the bladder to compress the measurement target part. The main body 3 measures pressure in the cuff (target object) 2 to calculate a blood pressure value of the user based on a measurement result. The fluid to be supplied from the main body 3 into the bladder is not particularly limited. Although the fluid may be liquid or gas, it is preferable that the fluid is the gas. For convenience of explanation, the following description will be given with assuming that the fluid is air.

When blood pressure is measured according to the general oscillometric method, the following procedure is performed. First, the cuff 2 is wound onto the measurement target part of the user. At the time of measuring the blood pressure, the air is supplied from the main body 3 into the cuff 2 to make the pressure in the cuff 2 (referred to as "cuff pressure") higher than a maximum blood pressure of the user. After that, the pressure in the cuff 2 is gradually reduced. During this process, the main body 3 detects the pressure in the cuff 2 to obtain a variation of an arterial volume occurring in an artery of the measurement target part as a pulse wave signal. The maximum blood pressure (systolic blood pressure) and a minimum blood pressure (diastolic blood pressure) of the user are calculated based on a change of an amplitude of the pulse wave signal caused by a change of the cuff pressure. More specifically, the maximum blood pressure (systolic blood pressure) and the minimum blood pressure (diastolic blood pressure) of the user are mainly calculated based on a rising edge and a falling edge of the pulse wave signal. However, the blood pressure measurement method is not particularly limited thereto. For example, it is possible to use the Riva-Rocci Korotkoff method commonly used in conjunction with the oscillometric method.

As shown in FIG. 1, the main body 3 contains a pump system 10 therein. The pump system 10 includes a pump 5 for supplying the air into the cuff 2 and a control device 6 for controlling drive of the pump 5 and detecting the pressure in the cuff 2. Further, as shown in FIG. 2, the pump 5 has a housing 7, a vibration actuator 8 and four pump units 9.

The vibration actuator 8 includes a shaft portion 81, a movable body 82 supported by the shaft portion 81 so as to be movable with respect to the housing 7 and a pair of coil core portions 85, 86 fixed to the housing 7.

The movable body 82 has an elongated shape. The movable body 82 is connected to the housing 7 so that a center portion of the movable body 82 is supported by the shaft portion 81. Thus, the movable body 82 can perform reciprocating rotation with respect to the housing 7 around the shaft portion 81 like a seesaw.

Magnets 83, 84 are respectively provided at both end portions of the movable body 82. The magnets 83, 84 are disposed so as to be symmetrical with each other across the shaft portion 81. The magnets 83, 84 respectively have arc-shaped magnetic pole faces 831, 841 respectively facing the coil core portions 85, 86. S poles and N poles are alternately arranged on each of the magnetic pole faces 831, 841 along its arc direction. Each of the magnets 83, 84 is a permanent magnet and composed of an Nd sintered magnet or the like.

Pushers 87, 88 are provided on the movable body 82 for pushing the pump units 9 when the movable body 82 performs the reciprocating rotation. The pushers 87, 88 are disposed so as to be symmetrically with each other across the shaft portion 81. The pusher 87 is disposed between the shaft portion 81 and the magnet 83 so as to protrude toward both sides in a width direction of the movable body 82 (both sides in the vertical direction in FIG. 2). Further, the pusher 88 is disposed between the shaft portion 81 and the magnet 84 so as to protrude toward both sides in the width direction of the movable body 82 (both sides in the vertical direction in FIG. 2).

The coil core portions 85, 86 are respectively disposed on both sides of the movable body 82. The coil core portion 85 faces the magnetic pole face 831 of the magnet 83. The coil core portion 86 faces the magnetic pole face 841 of the magnet 84. The coil core portions 85, 86 are disposed so as to be symmetrical with each other across the shaft portion 81.

The coil core portion 85 includes a core portion 851 and a coil 859 wound around the core portion 851. The core portion 851 has a core 852 around which the coil 859 is wound and a pair of core magnetic poles 853, 854 respectively extending from both ends of the core 852. The core magnetic poles 853, 854 respectively have magnetic pole faces 853a, 854a facing the magnetic pole face 831 of the magnet 83. Each of the magnetic pole faces 853a, 854a is curved in an arc shape so as to correspond to a shape of the magnetic pole face 831 of the magnet 83. The coil 859 is connected to the control device 6. When electric power is supplied to the coil 859 from the control device 6, the core magnetic poles 853, 854 are excited with different polarities.

The coil core portion 86 includes a core portion 861 and a coil 869 wound around the core portion 861. The core portion 861 has a core 862 around which the coil 869 is wound and a pair of core magnetic poles 863, 864 respectively extending from both ends of the core 862. The core magnetic poles 863, 864 respectively have magnetic pole faces 863a, 864a facing the magnetic pole face 841 of the magnet 84. Each of the magnetic pole faces 863a, 864a is curved in an arc shape so as to correspond to a shape of the magnetic pole face 841 of the magnet 84. The coil 869 is connected to the control device 6. When the electrical power is supplied to the coil 869 from the control device 6, the core magnetic poles 863, 864 are excited with different polarities.

The core portions 851, 861 are respectively magnetic material which can be respectively magnetized by supplying the electric power to the coils 859, 869. For example, each of the core portions 851, 861 can be formed from electromagnetic stainless steel, sintered material, MIM (metal injection mold) material, a laminated steel sheet, an electrogalvanized steel sheet (SECC) or the like.

The four pump units 9 are respectively disposed on an upper left side, an upper right side, a lower left side and a lower right side of the shaft portion 81. Specifically, two of the pump units 9 are disposed so as to face each other in the vertical direction across the pusher 87. Further, remaining two of the pump units 9 are disposed so as to face each other in the vertical direction across the pusher 88. The four pump units 9 have the same configuration as each other. Each of the pump units 9 has a sealed chamber 91 and a movable wall 92.

The sealed chamber 91 is connected to a suction port 98 for sucking the air from the outside into the sealed chamber 91 and a discharge port 99 for discharging the air in the sealed chamber 91 toward the outside. In the present embodiment, two of the sealed chambers 91 located on the upper side of the movable body 82 share one discharge port 99. Remaining two of the sealed chambers 91 located on the lower side of the movable body 82 share another discharge port 99.

The movable wall 92 constitutes a part of the sealed chamber 91. The movable wall 92 can be displaced to change a volume in the sealed chamber 91 when the movable wall 92 is pushed by the pusher 87 or 88. When the volume in the sealed chamber 91 reduces due to displacement of the movable wall 92, the air in the sealed chamber 91 is discharged from the discharge port 99. On the other hand, when the volume in the sealed chamber 91 increases due to the displacement of the movable wall 92, the air flows into the sealed chamber 91 through the suction port 98. When the above-mentioned reduction and increase of the volume in each of the sealed chambers 91 are repeated, the air is continuously discharged from the discharge ports 99. The movable walls 92 may be a diaphragm, for example. The movable wall 92 can be formed from elastically deformable material. Each of the movable walls 92 has an insertion portion 921 into which the pusher 87 or 88 should be inserted. Each of the movable walls 92 is connected to the pusher 87 or 88 through the insertion portion 921.

Valves 93 are respectively provided between the sealed chambers 91 and the suction ports 98. Each of the valves 93 allows the air to be suctioned into each of the sealed chambers 91 through the suction port 98 and prevents the air from being discharged from each of the sealed chambers 91 through the suction port 98. Further, valves 94 are respectively provided between the sealed chambers 91 and the discharge ports 99. Each of the valves 94 allows the air to be discharged from each of the sealed chambers 91 through the discharge port 99 and prevents the air from being suctioned into each of the sealed chambers 91 through the discharge port 99. With this configuration, it is possible to more reliably and more efficiently perform the suction and the discharge of the air.

As shown in FIG. 1, the control device 6 has a drive control unit 61 for controlling the drive of the vibration actuator 8 and a pressure detection unit 62 for detecting the pressure in the cuff 2. The control device 6 is composed of a computer or the like. The control device 6 has a processor (CPU) for processing information, a memory communicatively connected to the processor and an external interface. In addition, the memory stores various programs which can be executed by the processor and the processor can read and execute the various programs stored in the memory.

The configuration of the electronic sphygmomanometer 1 has been described. Next, the drive of the pump 5 will be described. In the following description, the four pump units 9 are distinguished from each other by labeling them as the "pump unit 9A", the "pump unit 9B", the "pump unit 9C" and the "pump unit 9D" for convenience of explanation.

When an AC (alternating-current) voltage is applied from the drive control unit 61 to the coils 859, 869, the pump 5 is driven by repeatedly alternating between a first state in which the movable body 82 rotates toward one direction as shown in FIG. 3 and a second state in which the movable body 82 rotates toward another direction as shown in FIG. 4. In the first state shown in FIG. 3, the core magnetic poles 853, 864 are excited with the N pole and the core magnetic poles 854, 863 are excited with the S pole. Conversely, in the second state shown in FIG. 4, the core magnetic poles 853, 864 are excited with the S pole and the core magnetic poles 854, 863 are excited with the N pole.

In the first state, torque F1 directed toward an arrow direction illustrated in FIG. 3 is generated by magnetic force (attractive force and repulsive force) acting between the magnets 83, 84 and the coil core portions 85, 86, and thereby the movable body 82 rotates in the direction of the torque F1. With this movement, the movable walls 92 of the pump units 9A, 9D are respectively pushed by the pushers 87, 88, and thereby the volumes in the sealed chambers 91 of the pump units 9A, 9D are reduced. As a result, the air in the sealed chambers 91 of the pump units 9A, 9D is discharged from the discharge ports 99. Further, the discharged air is supplied into the cuff 2 through the tube 4, and thereby the pressure in the cuff 2 increases. On the other hand, since the volumes in the sealed chambers 91 of the pump units 9B, 9C increase, the air flows into the sealed chambers 91 of the pump units 9B, 9C through the suction ports 98.

In the second state, torque F2 directed toward a direction opposite to the direction of the torque F1 is generated by the magnetic force (attractive force and repulsive force) acting between the magnets 83, 84 and the coil core portions 85, 86, and thereby the movable body 82 rotates in the direction of the torque F2. With this movement, the movable walls 92 of the pump units 9B, 9C are respectively pushed by the pushers 87, 88, and thereby the volumes in the sealed chambers 91 of the pump unit 9B, 9C are reduced. As a result, the air in the sealed chambers 91 of the pump unit 9B, 9C is discharged from the discharge ports 99. Further, the discharged air is supplied into the cuff 2 through the tube 4, and thereby the pressure in the cuff 2 increases. On the other hand, since the volumes in the sealed chambers 91 of the pump units 9A, 9D increase, the air flows into the sealed chambers 91 of the pump units 9A, 9D through the suction ports 98.

As described above, when the pump 5 repeatedly alternates between the first state and the second state, it is possible to repeatedly alternate the state in which the air is discharged from the pump units 9A, 9D and the state in which the air is discharged from the pump units 9B, 9C. As a result, the air can be continuously discharged from the pump 5. Therefore, it is possible to efficiently supply the air into the cuff 2 and smoothly increase the pressure in the cuff 2.

The drive of the pump 5 has been explained in the above description. Next, a driving principle of the pump 5 will be explained. The vibration actuator 8 is driven according to a motion equation expressed by the following equation (1) and a circuit equation expressed by the following equation (2).

[Equation 1]

$$J\frac{d^2\theta(t)}{dt^2} = K_t(i) - K_{sp}\theta(t) - D\frac{d\theta(t)}{dt} \qquad (1)$$

J: Inertial moment [Kg*m$^2$]
θ(t): Displacement angle [rad]
$K_t$: Torque constant [Nm/A]
i(t): Current[A]
$K_{sp}$: Spring constant [N/m]
D: Damping coefficient [Nm/(rad/s)]

[Equation 2]

$$e(t) = Ri(t) + L\frac{di(t)}{dt} + K_e\frac{dx(t)}{dt} \qquad (2)$$

e(t): Voltage [V]
R: Resistance [Ω]
L: Inductance [H]
$K_e$: Counter-electromotive force constant [V/(m/s)]

As described above, the inertial moment J [Kg*m$^2$], the displacement angle (rotational angle) θ(t) [rad], the torque constant $K_t$ [Nm/A], the current i(t) [A], the spring constant $K_{sp}$ [N/m], the damping coefficient D [Nm/(rad/s)] and the like of the movable body 82 can be appropriately set as long as they satisfy the equation (1). Similarly, the voltage e(t) [V], the resistance R [Ω], the inductance L [H] and the counter-electromotive force constant $K_e$ [V/(m/s)] can be appropriately set as long as they satisfy the equation (2).

Further, a flow rate of the pump 5 is determined by the following equation (3) and pressure of the pump 5 is determined by the following equation (4).

[Equation 3]

$$Q = Axf*60 \qquad (3)$$

Q: Flow rate [L/min]
A: Piston area [m$^2$]
x: Piston displacement [m]
f: Drive frequency [Hz]

[Equation 4]

$$P = P_0\left(\frac{V + \Delta V}{V - \Delta V} - 1\right) \qquad (4)$$

P: Increased pressure [kPa]
$P_0$: Atmospheric pressure [kPa]
V: Sealed chamber volume [m$^3$]
ΔV: Changed volume [m$^3$]
ΔV=Ax
A: Piston area [m$^2$]
x: Piston displacement [m]

As described above, the flow rate Q [L/min], the piston area A [m$^2$], the piston displacement x [m], the drive frequency f [Hz] and the like of the pump 5 can be appropriately set as long as they satisfy the equation (3). Similarly, the increased pressure P [kPa], the atmospheric pressure $P_0$ [kPa], the sealed chamber volume V [m$^3$], the changed volume ΔV [m$^3$] and the like can be appropriately set as long as they satisfy the equation (4).

Next, a resonance frequency of the vibration actuator 8 will be explained. As shown in FIG. 5, the vibration actuator 8 has a spring mass system structure for supporting the movable body 82 by magnetic springs B1 formed by the magnetic force acting between the coil core portions 85, 86 and the magnets 83, 84 and air springs (fluid springs) B2 formed by elastic force of compressed air in the sealed chambers 91. Thus, the movable body 82 has a resonant frequency $f_r$ expressed by the following equation (5).

[Equation 5]

$$f_r = \frac{1}{2\pi}\sqrt{\frac{K_{sp}}{J}} \qquad (5)$$

$f_r$: Resonance frequency [Hz]
$K_{sp}$: Spring constant [N/m]
J: Inertial moment [kg*m$^2$]

Further, the spring constant $K_{sp}$ can be expressed by a sum of a spring constant $K_{ACT}$ of the vibration actuator 8 itself, which contains the effects of the magnetic springs B1 and elastic force B3 of the movable walls 92, and a spring constant $K_{Air}$ of the air springs B2 as expressed by the following equation (6).

[Equation 6]

$$K_{sp} = K_{ACT} + K_{Air} \qquad (6)$$

$K_{ACT}$: Spring constant of vibration actuator itself
$K_{Air}$: Spring constant of air spring In the vibration actuator 8, the spring constant $K_{Air}$ of each air spring B2 changes according to the pressure in each sealed chamber 91 (the pressure in the cuff 2) and thus the resonant frequency $f_r$ of the movable body 82 changes according to the change of the spring constant $K_{Air}$ as is clear from the above equations (5) and (6). Therefore, a change of consumption current (consumption power) of the vibration actuator 8 occurring according to the above-described change of the resonance frequency $f_r$ is utilized in the pump system 10 to detect the pressure in the sealed chambers 91 (the pressure in the cuff 2) based on this change of the consumption current of the vibration actuator 8.

Next, a pressure detection method based on the consumption current (consumption power) of the vibration actuator 8 will be described in detail. The following description will be given to a representative example in which the pump 5 can increase the pressure in the cuff 2 up to 50 kPa at the maximum for convenience of explanation. It is noted that the maximum value of the pressure in the cuff 2 is not particularly limited and can be appropriately set so as to meet required conditions. Further, since the cuff 2 is connected to the sealed chambers 91 through the tube 4 as described above, the pressure in the cuff 2 is equal to the pressure in each sealed chamber 91. Thus, the meaning of the "pressure in the sealed chamber(s) 91" and the meaning of the "pressure in the cuff 2" are synonymous with each other.

FIG. 6 shows a relationship between the drive frequency f and the consumption current of the vibration actuator 8 when the pressure in the cuff 2 falls within the range between 0 kPa and 50 kPa. The "consumption current" of the vibration actuator 8 refers to a current flowing in a main circuit of the vibration actuator 8. Thus, the consumption current of the vibration actuator 8 refers to a current flowing mainly in a circuit for supplying the current to the coils 859, 869. Further, an AC voltage applied to the coils 859, 869 is constant. It should be noted that the relationship shown in FIG. 6 is merely one example and thus the present disclosure is not limited to this relationship.

In FIG. 6, the resonance frequency $f_r$ at each pressure substantially coincides with a value of the drive frequency f at which the consumption current becomes the smallest. Thus, it can be seen from FIG. 6 that the spring constant $K_{Air}$ of each air spring B2 increases and thus the resonant frequency $f_r$ is shifted to the higher side as the pressure in the cuff 2 increases.

Here, in FIG. 6, the consumption current of the vibration actuator 8 reduces in an area where the drive frequency f falls within the range between $f_{min}$ and $f_{max}$ as the pressure in the cuff 2 increases. Namely, the consumption current monotonically changes (in one of a reducing direction and an increasing direction) as the pressure in the cuff 2 increases. The pump 5 is configured so that the drive frequency f is set so as to be in a range in which the consumption current monotonically changes as the pressure in the cuff 2 increases, such as an illustrated range between $f_{min}$ and $f_{max}$. In this regard, the drive frequency f may be fixed at an arbitrary initial value so that the drive frequency f cannot be changed. Alternatively, the user may appropriately set the drive frequency f within the range between $f_{min}$ and $f_{max}$. The following description will be given to a representative example in which the drive frequency f is fixed at a frequency $f_n$ for convenience of explanation.

Figure 7:
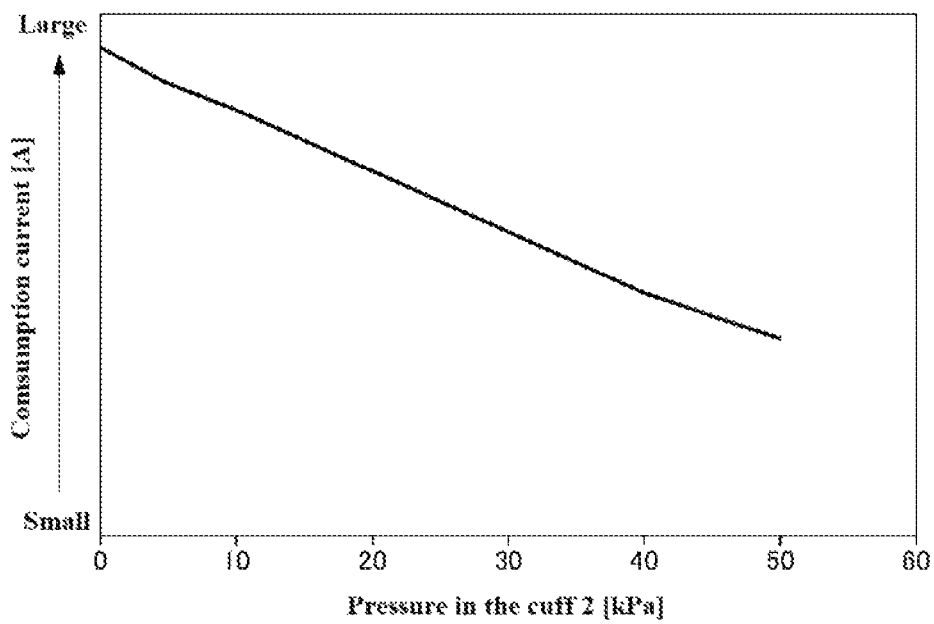
FIG. 7 is a graph showing a relationship between pressure in a sealed chamber and the consumption current.

FIG. 7 shows a relationship between the pressure in the sealed chamber 91 and the consumption current of the vibration actuator 8 when the drive frequency f is set to the frequency $f_n$ (f=$f_n$). As shown in FIG. 7, when the drive frequency f is set to the frequency $f_n$, the consumption current of the vibration actuator 8 linearly reduces as the pressure in the cuff 2 increases.

The relationship between the pressure in the cuff 2 and the consumption current of the vibration actuator 8 when the drive frequency f is set to the frequency $f_n$ (f=$f_n$) is stored in the pressure detection unit 62 of the control device 6 as a table or a calculation formula (function) in advance. Further, the pressure detection unit 62 detects the consumption current of the vibration actuator 8 and applies the detected consumption current to the table or function stored therein to obtain the pressure in the cuff 2. In particular, since the consumption current of the vibration actuator 8 linearly reduces in the present embodiment, a degree of the change of the consumption current with respect to the pressure in the cuff 2 is substantially uniform and sufficiently large in the entire area of the pressure range between 0 kPa and 50 kPa. Therefore, it is possible to accurately detect the pressure in the cuff 2 in the entire area of the pressure.

As described above, according to the pump system 10, it is possible to detect the pressure in the cuff 2 by utilizing the characteristic of the pump 5 itself and without using any pressure sensor. Thus, it becomes unnecessary to provide any additional component such as a pressure sensor for detecting the pressure in the cuff 2 separately from the pump 5 unlike the conventional art. Therefore, it is possible to reduce the number of components of the pump system 10 and reduce the size of the pump system 10. In particular, since the vibration actuator 8 has the characteristic that the resonance frequency $f_r$ changes according to the pressure in the cuff 2, it is possible to easily allow the vibration actuator 8 to have the characteristic that the consumption current changes according to the change of the pressure in the cuff 2. In addition, since the vibration actuator 8 has the air springs B2, it is possible to allow the vibration actuator 8 to have the characteristic that the resonance frequency $f_r$ changes according to the pressure in the cuff 2 with a simple configuration.

A method for setting the drive frequency f is not particularly limited. For example, the drive frequency f can be set according to the following procedure. As the drive frequency f becomes closer to the resonance frequency $f_r$, the amplitude of the vibration actuator 8 becomes larger. Thus, it is possible to increase the flow rate Q of the air discharged from the pump 5. Further, as the drive frequency f becomes closer to the resonance frequency $f_r$, the power saving drive of the vibration actuator 8 becomes possible. On the other hand, as a difference between a consumption current of the vibration actuator 8 when the pressure is 0 kPa and a consumption current of the vibration actuator 8 when the pressure is 50 kPa becomes larger, the degree of the change of the consumption current with respect to the pressure in the cuff 2 becomes larger. Thus, it becomes possible to more accurately detect the pressure in the cuff 2.

Therefore, it is preferable that the drive frequency f is set at a frequency value which is within the range between the resonance frequency $f_r$ when the pressure is 0 kPa and the resonance frequency $f_r$ when the pressure is 50 kPa and at which the difference between the consumption current when the pressure is 0 kPa and the consumption current when the pressure is 50 kPa becomes maximum or the drive frequency f is set in a vicinity of this frequency value (for example, a range in which the difference is equal to or more than 90% of a maximum value of the difference). By setting the drive frequency f so as to satisfy the above conditions, it becomes possible to efficiently drive the pump 5 as well as more accurately detect the pressure in the cuff 2. For the reasons stated above, the drive frequency f in the present embodiment is set at the frequency $f_n$ which is within the range between the resonance frequency $f_r$ when the pressure is 0 kPa and the resonance frequency $f_r$ when the pressure is 50 kPa and at which the difference between the consumption current when the pressure is 0 kPa and the consumption current when the pressure is 50 kPa becomes maximum.

Figure 8:
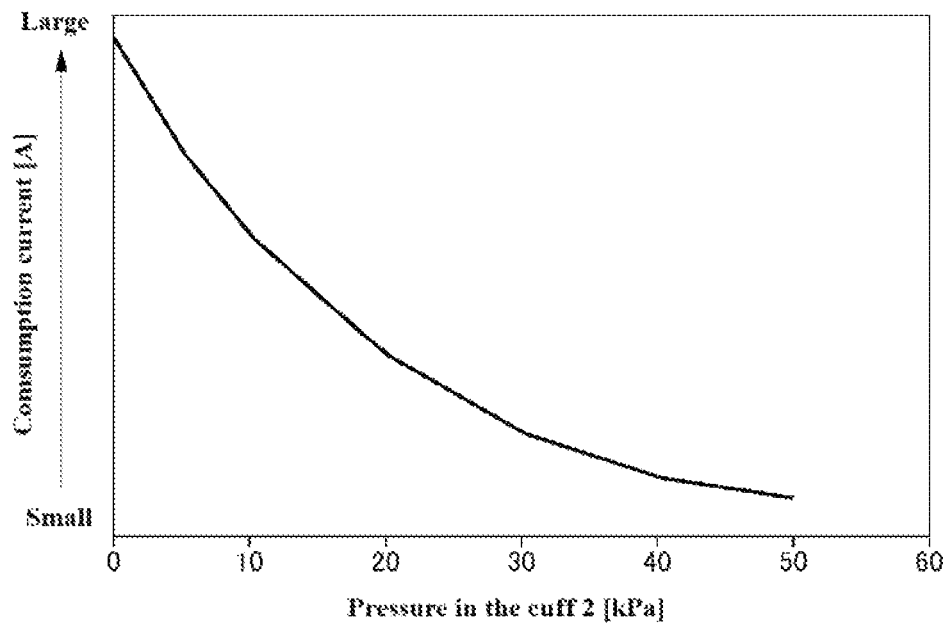
FIG. 8 is a graph showing another relationship between the pressure in the sealed chamber and the consumption current.

In this regard, although the consumption current of the vibration actuator 8 in FIG. 7 linearly reduces as the pressure in the cuff 2 increases, the change of the consumption current of the vibration actuator 8 is not limited thereto. For example, the vibration actuator 8 may be configured so that the consumption current of the vibration actuator 8 nonlinearly reduces as shown in FIG. 8. In this case, since the degree of the change of the consumed current with respect to the pressure is large in an area in which the pressure in the cuff 2 is low, it is possible to more accurately detect the pressure in the cuff 2. On the other hand, the degree of the change of the consumed current with respect to the pressure tends to be small in an area where the pressure in the cuff 2 is high. Thus, there is a possibility that the pressure in the cuff 2 cannot be detected with sufficient accuracy. For this reason, the configuration providing the linear characteristic shown in FIG. 7 is better.

Figure 9:
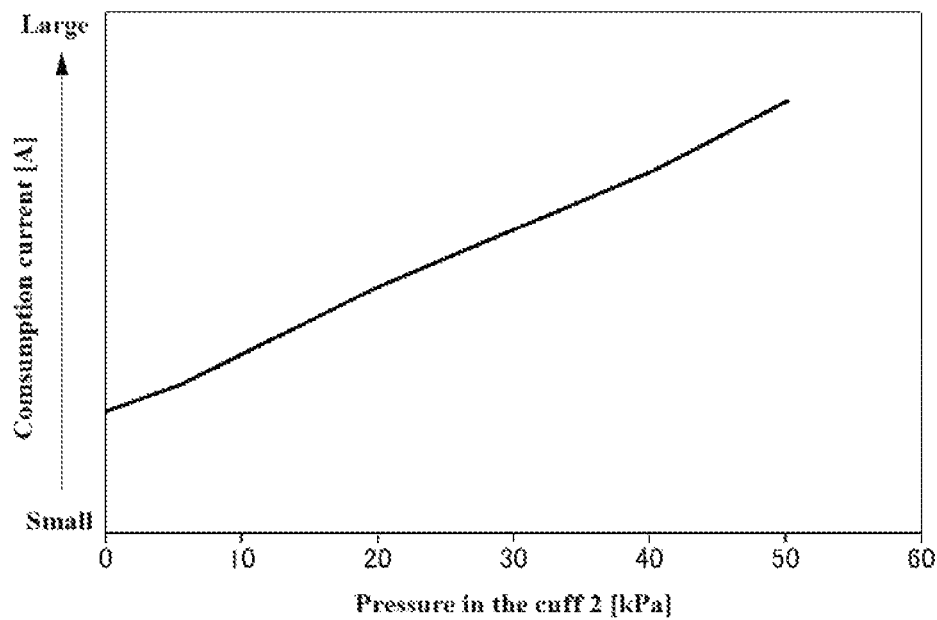
FIG. 9 is a graph showing yet another relationship between the pressure in the sealed chamber and the consumption current.

Further, although the consumption current of the vibration actuator 8 in FIG. 7 monotonically changes in the reducing direction as the pressure in the cuff 2 increases, the change of the consumption current of the vibration actuator 8 is not limited thereto. For example, the vibration actuator 8 may be configured so that the consumption current of the vibration actuator 8 monotonically changes in the increasing direction as the pressure in the cuff 2 increases as shown in FIG. 9. Even in this case, the degree of the change of the consumption current with respect to the pressure in the cuff 2 is also sufficiently large in the entire area of the pressure similar to the case shown in FIG. 7. Therefore, it is possible to accurately detect the pressure in the cuff 2 in the entire area of the pressure.

Figure 10:
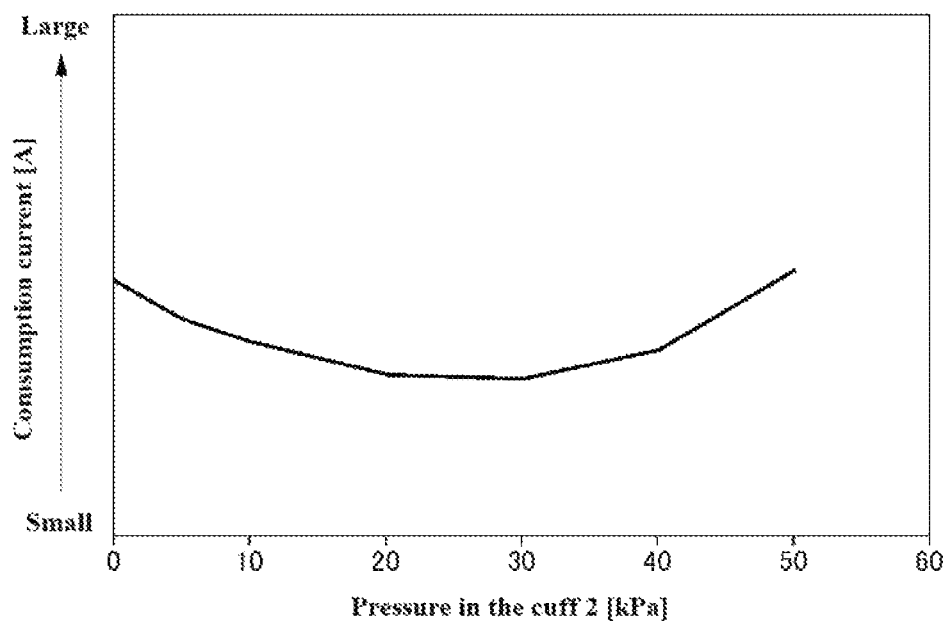
FIG. 10 is a graph showing yet another relationship between the pressure in the sealed chamber and the consumption current.
Figure 11:
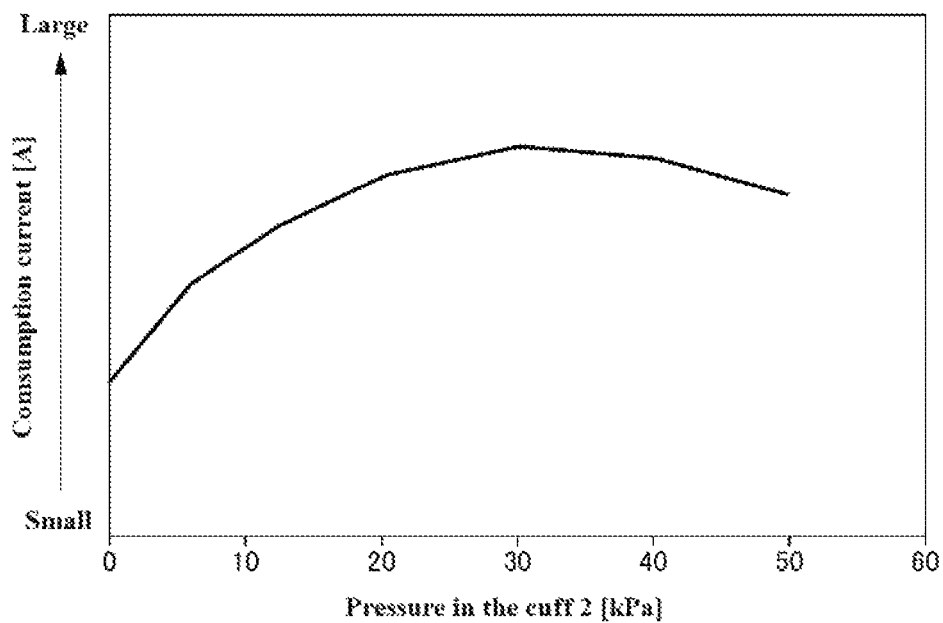
FIG. 11 is a graph showing yet another relationship between the pressure in the sealed chamber and the consumption current.

Further, although the consumption current of the vibration actuator 8 in FIG. 7 monotonically changes in the reducing direction as the pressure in the cuff 2 increases, the change of the consumption current of the vibration actuator 8 is not limited thereto. For example, the vibration actuator 8 may be configured so that the consumption current of the vibration actuator 8 changes so as to increase after it has decreased as shown in FIG. 10 or changes so as to decrease after it has increased as shown in FIG. 11. However, since there are cases where the same consumption current can be provided from different pressure values across its extreme value in this case, it is necessary to provide modification for distinguishing these pressure values. For example, the consumption current may be continuously detected from a state that the pressure is sufficiently low to determine whether or not the consumption current exceeds the extreme value (a local minimum value in the case of FIG. 10 or a local maximum value in the case of FIG. 11). Based on this determination result, it is possible to determine whether the pressure is on the side lower than the extreme value or on the side higher than the extreme value.

Further, although the above description has been given to the case in which the drive frequency f is fixed at the frequency $f_n$, the present disclosure is not limited thereto. For example, if the user can appropriately select the drive frequency f from a plurality of values, the pressure detection unit 62 may store relationships between the pressure in the cuff 2 and the consumption current for each selectable values of the drive frequency f as tables or functions and the table or the function corresponding to selected one value of the drive frequency f can be used to obtain the pressure in the cuff 2.

Although the pump system, the fluid supply device and the pressure detection method of the present disclosure have been described based on the illustrated embodiment, the present disclosure is not limited thereto. The configuration of each part can be replaced with any configuration having a similar function. Further, other optional component(s) may be also added to the present disclosure.

In addition, although the pump system and the fluid supply device are applied to the electronic sphygmomanometer 1 in the above-described embodiment, the present disclosure is not limited thereto. For example, the pump system and the fluid supply device can be applied to any device which requires the supply of fluid. Further, although the pump 5 has the four pump units 9 in the above-described embodiment, the present disclosure is not limited thereto. For example, the present disclosure involves an aspect in which the pump 5 has at least one pump unit 9.

Further, the configuration of the vibration actuator 8 is not particularly limited as long as the configuration of the vibration actuator 8 allows the consumption current to change according to the pressure in the sealed chamber(s) 91. For example, although the magnets 83, 84 are provided on the movable body 82 and the coil core portions 85, 86 are provided on the housing 7 in the above-described embodiment, the present disclosure is not limited thereto. The present disclosure involves an aspect in which the arrangement of the magnets 83, 84 and the arrangement of the coil core portions 85, 86 are reversed. Namely, the coil core portions 85, 86 may be provided on the movable body 82 and the magnets 83, 84 may be provided on the housing 7. Further, the magnets 83, 84 may be replaced with electromagnets.

The invention claimed is:

1. A pump system, comprising:
 a vibration actuator which can be electromagnetically driven;
 a pair of sealed chambers connected to a suction port and a discharge port;
 movable walls respectively changing volumes of the sealed chambers; and
 a housing containing the vibration actuator, the pair of sealed chambers and the movable walls therein,
 wherein the movable walls are displaced due to drive of the vibration actuator to respectively supply fluid in the pair of sealed chambers into a target object,
 wherein pressure in the target object is detected based on a consumption current of the vibration actuator,
 wherein the vibration actuator includes a shaft portion provided in the housing, a movable body supported by the shaft portion so that the movable body can perform reciprocating rotation with respect to the housing, a pair of coil core portions fixed to one of the housing and the movable body, and magnets provided on another of the housing and the movable body so as to respectively face the coil core portions,
 wherein a spring mass system structure for supporting the movable body is constituted of magnetic springs formed by magnetic force acting between the coil core portions and the magnets and fluid springs formed by elastic force of compressed fluid in the pair of sealed chambers, and
 wherein a drive frequency of the vibration actuator is set so as to be in a range in which the consumption current monotonically changes as the pressure in the target object increases.

2. The pump system as claimed in claim 1, wherein the vibration actuator is configured so that a resonant frequency of the vibration actuator changes according to the pressure in the target object.

3. The pump system as claimed in claim 1, wherein the consumption current linearly changes.

4. A fluid supply device, comprising:
 the pump system defined by claim 1.

5. The pump as claimed in claim 1, wherein the movable body has an elongated shape, and
 wherein the magnets are respectively provided at both end portions of the movable body in a longitudinal direction of the movable body.

6. The pump as claimed in claim 5, wherein the coil core portions are respectively disposed on both sides of the movable body in the longitudinal direction of the movable body so as to be symmetrical with each other across the shaft portion.

7. The pump as claimed in claim 1, wherein each of the magnets has an arc-shaped magnetic pole face,
   wherein each of the coil core portions has an arc-shaped magnetic pole face facing the arc-shaped magnetic pole face, and
   wherein the arc-shaped magnetic pole faces of the coil core portions respectively face the arc-shaped magnetic pole face of the magnets.

8. A pressure detection method performed by a pump system containing a vibration actuator which can be electromagnetically driven, a pair of sealed chambers connected to a suction port and a discharge port, movable walls respectively changing volumes of the pair of sealed chambers, and a housing containing the vibration actuator, the pair of sealed chambers and the movable walls therein, wherein the movable walls are displaced due to drive of the vibration actuator to respectively supply fluid in the pair of sealed chambers into a target object, the pressure detection method comprising:
   detecting consumption current of the vibration actuator; and
   calculating pressure in the target object from the detected consumption current of the vibration actuator based on a relationship between the pressure in the target object and the consumption current of the vibration actuator, wherein the relationship is stored in advance,
   wherein the vibration actuator includes a shaft portion provided in the housing, a movable body supported by the shaft portion so that the movable body can perform reciprocating rotation with respect to the housing, a pair of coil core portions fixed to one of the housing and the movable body, and magnets provided on another of the housing and the movable body so as to respectively face the coil core portions,
   wherein a spring mass system structure for supporting the movable body is constituted of magnetic springs formed by magnetic force acting between the coil core portions and the magnets and fluid springs formed by elastic force of compressed fluid in the pair of sealed chambers, and
   wherein a drive frequency of the vibration actuator is set so as to be in a range in which the consumption current monotonically changes as the pressure in the target object increases.

* * * * *